US00PP36388P2

(12) United States Plant Patent
Contreras

(10) Patent No.: US PP36,388 P2
(45) Date of Patent: Jan. 14, 2025

(54) ***STYRAX JAPONICUS* PLANT NAMED 'ORSTSTYx1'**

(50) Latin Name: *Styrax japonicus*
Varietal Denomination: ORSTSTYx1

(71) Applicant: Oregon State University, Corvallis, OR (US)

(72) Inventor: Ryan N. Contreras, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 18/241,074

(22) Filed: Aug. 31, 2023

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./216
See application file for complete search history.

*Primary Examiner* — Susan McCormick Ewoldt
(74) *Attorney, Agent, or Firm* — Klarquist Sparkman, LLP

(57) ABSTRACT

A new and distinct *Styrax japonicus* plant named 'ORSTSTYx1' is disclosed, characterized by its strict weeping habit, purple foliage, pink flowers, and vigorous growth.

5 Drawing Sheets

Latin name of the genus and species of the plant claimed: *Styrax japonicus.*

Variety denomination: 'ORSTSTYx1'.

BACKGROUND

The present application relates to a new and distinct variety of *Styrax japonicus* named 'ORSTSTYx1', which is an infraspecific hybrid resulting from a cross made in 2016 between *Styrax japonicus* 'Evening Light' (patented; U.S. Plant Pat. No. 24,168) as the female parent x *Styrax japonicus* 'JLWeeping' (patented; U.S. Plant Pat. No. 23,755) as the male parent. The original accession was designated H2017-001-002. The original seedling was field planted in 2018. Measurements from the original plant and were collected during spring 2023.

SUMMARY

Plants of the new *Styrax japonicus* have not been observed under all possible combinations of environmental conditions and cultural practices. However, the following traits have been consistently observed and are unique combinations of characteristics for 'ORSTSTYx1':

1. Strict weeping habit
2. Purple foliage
3. Pink flowers
4. Vigorous growth

Asexual reproduction of this new variety from chip budding, grafting, and tissue culture, shows that the foregoing characteristics come true to form, are firmly fixed, and are established and transmitted through succeeding propagations. Asexual reproduction was initially performed in Corvallis, Oregon, but has also been performed in Albany, Oregon, McMinnville, Oregon, and Middleton, Wisconsin.

Certain characteristics of this variety may change with changing environmental conditions (such as photoperiod, temperature, moisture, soil conditions, nutrient availability, or other factors). Thus, the phenotype may vary somewhat (particularly colors) with variations in environmental conditions without any variance in genotype. Color descriptions and other terminology are used in accordance with their ordinary dictionary descriptions, unless the context clearly indicates otherwise. Color designations (hue/value/chroma) are made with reference to The Royal Horticultural Society Colour Chart (R.H.S) 5$^{th}$ edition, 2007. Color values were determined under natural light conditions in Corvallis, Oregon.

Figure 1:
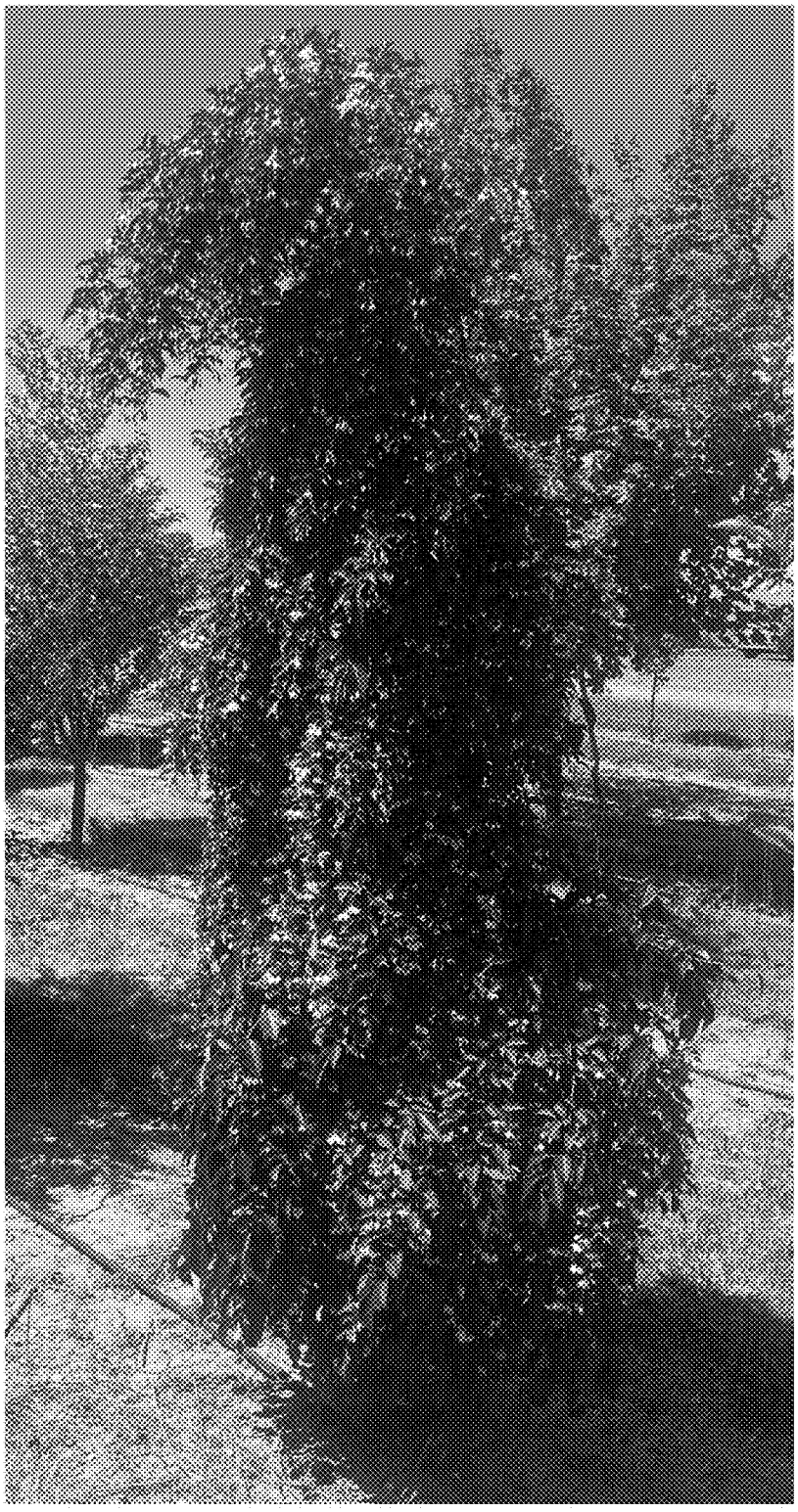
FIG. 1 is a photograph of the original plant of 'ORSTSTYx1' growing in a field in Corvallis, OR. The photo was taken on Jun. 3, 2023.
Figure 2:
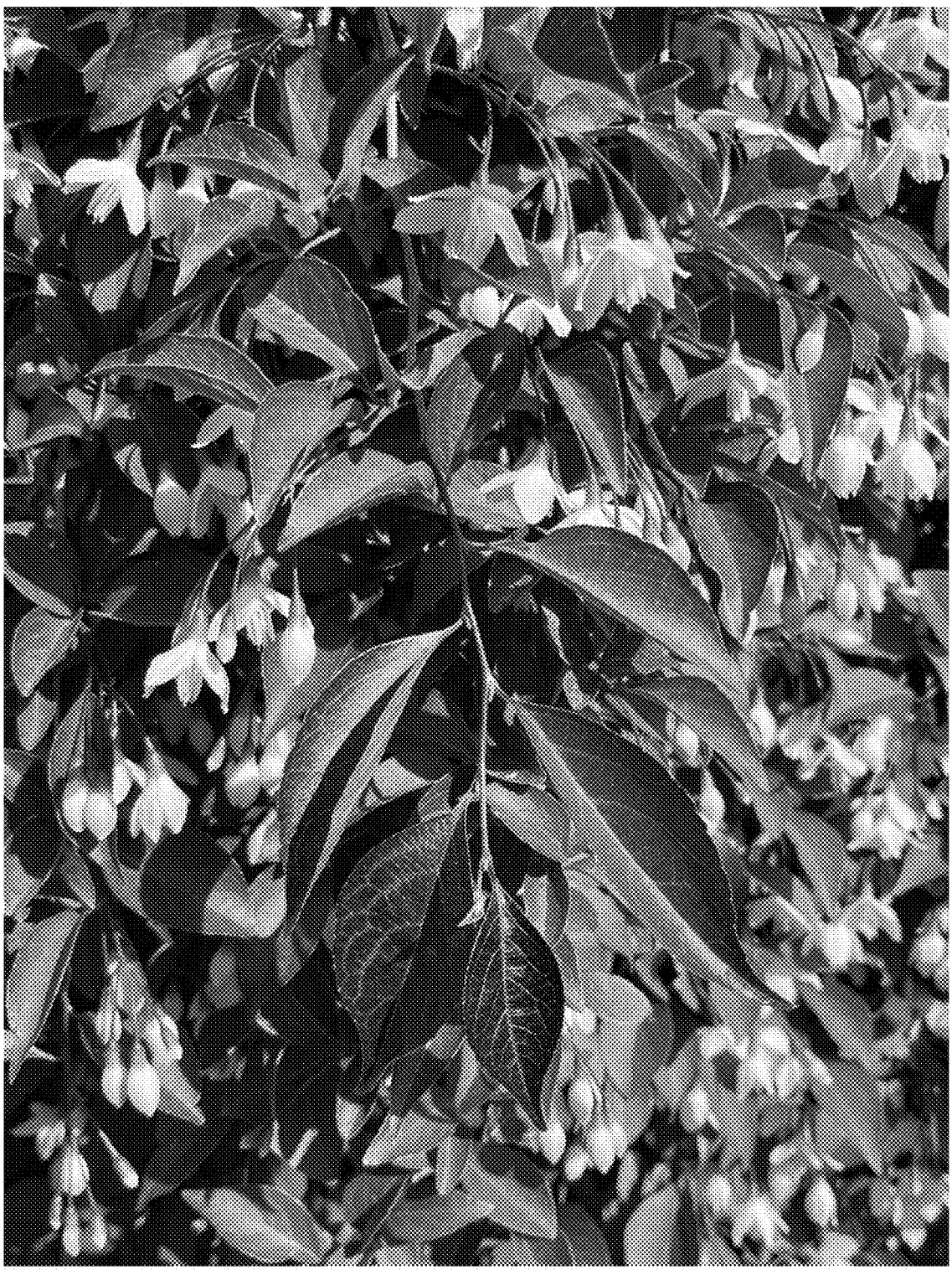
FIG. 2 is a photograph of 'ORSTSTYx1' exhibiting its flowers and dark foliage. Initial foliage emerges green during early spring and subsequently develops to a characteristic dark foliage. Flowers are distinctly pink in bud and open to a blush pink. The photo was taken on Jun. 3, 2023.
Figure 3:
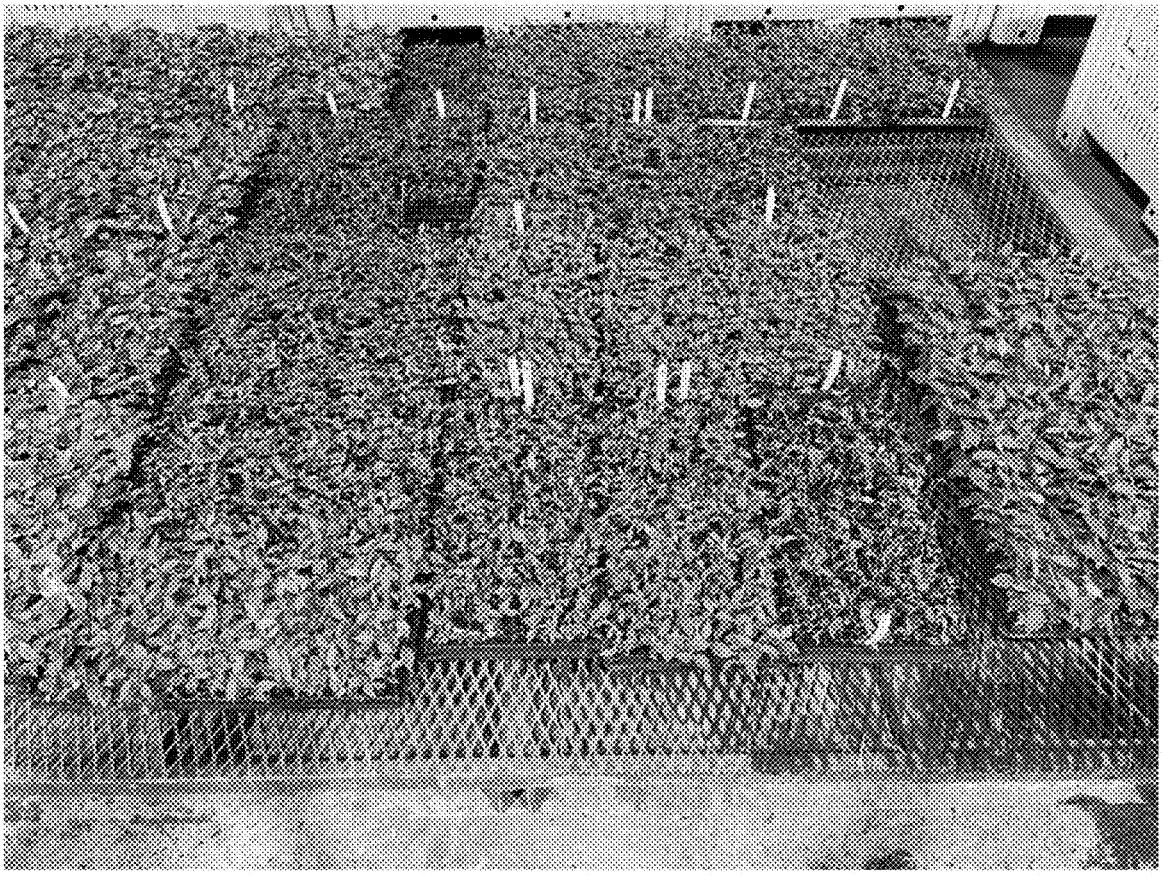
FIG. 3 is a photograph illustrating liner production of 'ORSTSTYx1'in Amity, OR. The plants were initially micropropagated (tissue culture propagation) in Middleton, WI. The photo was taken on Apr. 25, 2023.
Figure 4:
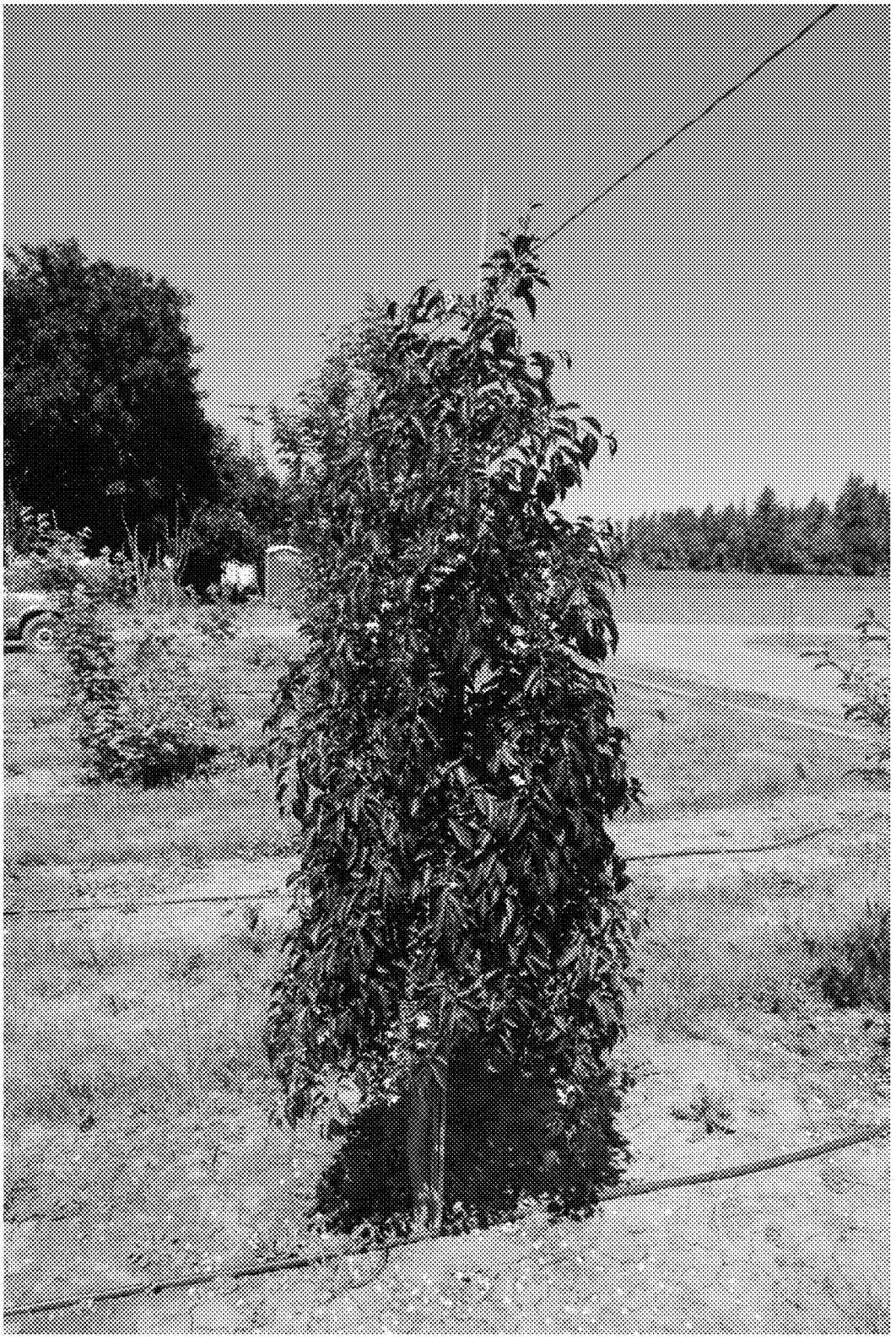
FIG. 4 is a photograph of the original plant of 'ORSTSTYx1' growing in the field in Corvallis, OR. The photo was taken on Jul. 7, 2021.
Figure 5:
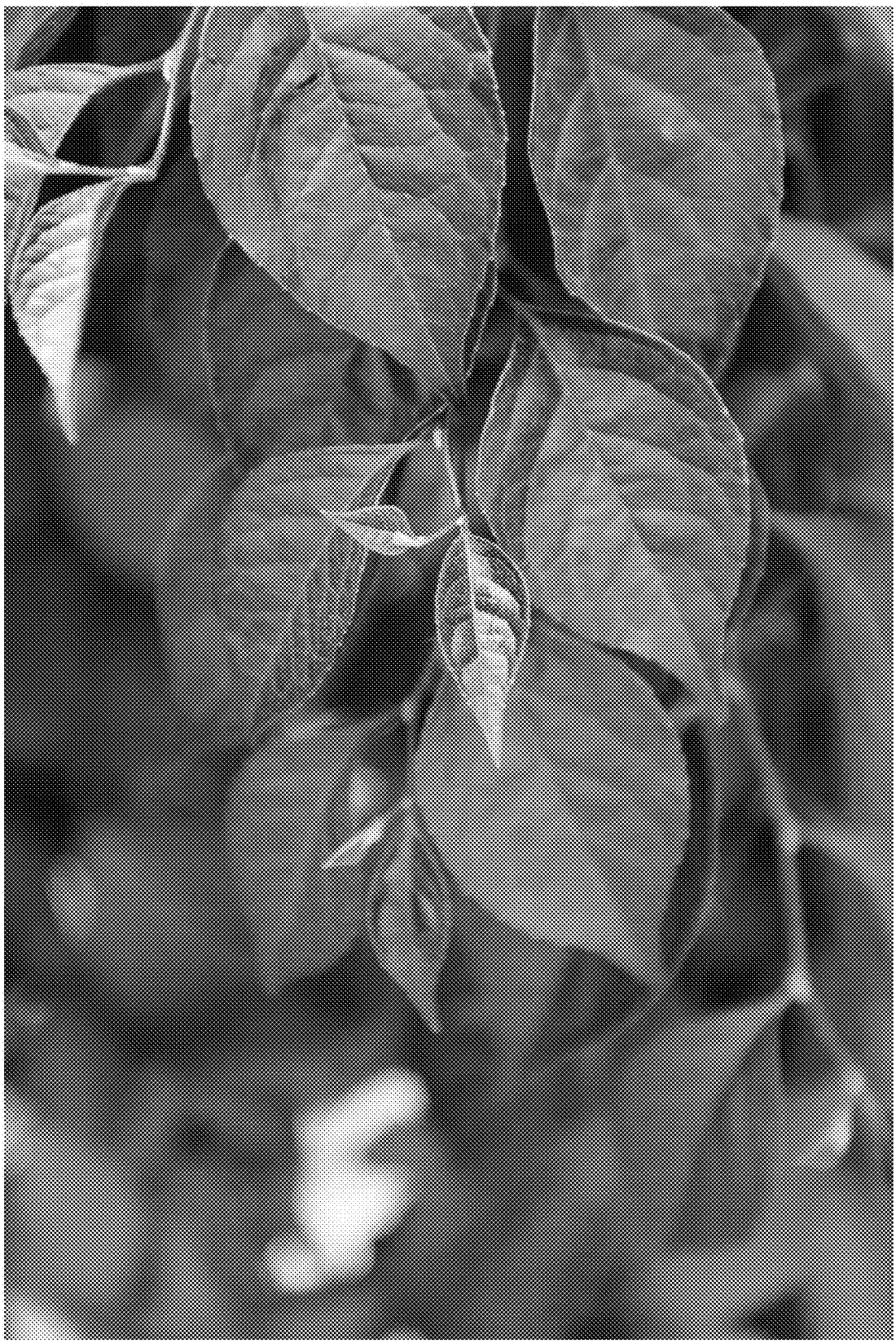
FIG. 5 is a photograph of 'ORSTSTYx1' exhibiting mature, dark foliage. The photo was taken on Jul. 7, 2021.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photographs alone.

DETAILED DESCRIPTION

The following is a detailed description while observing the original seedling as a mature plant in the field. The plant was grown as a seedling for two years and then field planted. At the time of observation, the plant was seven years from seed and had been field-grown for five years. Flowering data was collected during June 2023. Plants were observed growing outdoors in full sun in Corvallis, Oregon.

Botanical Description

Table 1 provides a comparison of 'ORSTSTYx1' to its female parent, 'Evening Light' and male parent, 'JLWeeping'. Measurements for 'Evening Light' and 'JLWeeping' were taken from plants that were container-grown in 2014 and field planted in 2018. These data generally allow discernment between 'ORSTSTYx1' and its parents on the basis that 'ORSTSTYx1' has purple foliage and is weeping. The female parent, 'Evening Light', has purple foliage but upright growth form. The male parent, 'JLWeeping', has green foliage and weeping habit. The only known cultivar having a related phenotype is *Styrax japonicus* 'JFS 6SJ' (U.S. Plant Pat. No. 34,817), however, it is distinguishable at least on the basis that it has white flowers while 'ORSTSTYx1' has pink flowers.

TABLE 1 comparison of 'ORSTSTYx1' to its female parent, 'Evening Light' and male parent, 'JL Weeping'

| | Color | | |
|---|---|---|---|
| | 'ORSTSTYx1' | 'Evening Light' | 'JL Weeping' |
| Purple young leaf adaxial | N200A | N200A | — |
| Purple young leaf abaxial | N200B | N200A | — |
| Purple expanded leaf adaxial | N200A | 200A | — |
| Purple expanded leaf abaxial | N200A | N200A | — |
| Green young leaf adaxial | 144A | 146B | 144A |
| Green young leaf abaxial | 146B | 146B | 146B |
| Green expanded leaf adaxial | N137B | N200A | N137B |
| Green expanded leaf abaxial | 146A | 147A | 137B |
| Petals | NN155C with 62D blush | NN155B | NN155B and 63A blush |
| Flower bud | N155D body with 62C blush | NN155B and N155C blush | NN155B and 63A blush |
| | Size (L × W unless otherwise indicated) | | |
| | 'ORSTSTYx1' | 'Evening Light' | 'JL Weeping' |
| Leaf | 29-77 mm × 18-40 mm | 27-45 mm × 17-24 mm | 37-65 mm × 21-34 mm |
| Flower diameter | 21.3 mm | 12.8 mm | 26 mm |
| Petal | 15 mm × 9.1 mm | 13.4 mm × 6 mm | 13.5 mm × 9.64 mm |
| Inflorescence length | 70.1 mm | 60.4 mm | 61.5 mm |

Parentage:

*Female parent.*—*Styrax japonicus* 'Evening Light', an upright, purple leaved cultivar.

*Male parent.*—*Styrax japonicus* 'JLWeeping', a green leaved weeping cultivar.

Plant:

*Growth habit.*—Weeping.

*Height.*—7.6 feet after 5 years in field and 7 years from seed.

*Trunk diameter.*—64 mm when measured about 1 ft above ground level.

*Hardiness.*—Expected to be hardy to USDA 5.

*Branch texture and color.*—Smooth, color is 199A.

Leaf:

*Arrangement.*—Alternate.

*Sheen.*—Smooth, both leaf surfaces glossy.

*Shape of leaf blade.*—Elliptic.

*Apex.*—Acuminate.

*Base.*—Cuneate.

*Margin.*—Serrate.

*Texture adaxial.*—Glossy.

*Texture abaxial.*—Glossy.

*Length.*—29-77 mm.

*Width.*—18-40 mm.

*Internode length.*—16-26 mm.

*Venation pattern.*—Reticulate.

*Vein color.*—200B adaxially and 200C abaxially.

*Petiole length.*—7.4 mm.

*Petiole diameter.*—1.1 mm.

*Petiole color.*—144A.

*Petiole texture.*—Smooth.

*Emerging leaf color.*—Young purple leaves are N200A on the adaxial surface and N200B on the abaxial surface. Emerging green leaves are 144A on the adaxial surface and 146B on the abaxial surface.

*Expanded leaf color.*—Fully expanded purple leaves are N200A on both adaxial and abaxial surfaces of the leaf. Fully expanded green leaves are N137B on the adaxial surface and 146A on the abaxial surface.

Flower:

*Shape.*—Campanulate.

*Size.*—21.3 mm diameter and 18.6 mm long when measured from tip of anther to bottom of calyx.

*Petals.*—5 per flower with entire margins; ovoid in shape, with color NN155C and 62D blush on the abaxial and adaxial surfaces. 9.1 mm wide and 15 mm long. Texture is smooth on both surfaces.

*Sepals.*—Short, pointed and largely fused to calyx. 2.7 mm long and 4 mm wide. Color is like 48A on tips. Apex is acute, base is fused to calyx and texture is glabrous.

*Pedicel.*—17.9 mm long, 0.71 mm in diameter; color is N34A.

*Peduncle.*—62.6 mm long, 1.4 mm in diameter. Color is 144B with slight blush like 178A. Texture is smooth with small lenticels.

*Fragrance.*—Lightly green-floral.

*Flowering season.*—May 31$^{st}$ to mid-June in 2023. In a typical year, flowering would occur approximately two weeks earlier.

*Flower longevity.*—Individual flowers last approximately 1-2 weeks.

*Persistence.*—Not persistent.

*Inflorescence.*—Form is a pendulous raceme, with flowers alternately arranged. There are generally 5 flowers per inflorescence.

*Terminal flower buds.*—18.2 mm long and 7 mm in diameter. Color at balloon stage is N155D with 62C blush. Texture is smooth and shape is ovoid.

*Lateral flower buds.*—15.6 mm long and 5.3 mm in diameter. Color at balloon stage is N155D with 62C blush. Texture is smooth and shape is ovoid.

Reproductive organs:

*Pistil.*—Singular; 12.6 mm long with smooth texture.

*Ovary.*—Rounded, inferior ovary is 3.14 mm long and 1.29 mm in diameter. Color is NN155D.

*Stigma.*—0.10 mm long and 1.29 mm in diameter; color is 155A.

*Style.*—Single linear style is 12.5 mm in length, 0.66 mm in diameter; color is 155A.

*Stamen.*—Flowers produce 6 stamens. Filaments are 3.87 mm in length and 1.68 mm in diameter; color is NN155D.

*Anthers.*—Linear in shape, 5.58 mm long and 0.91 mm in diameter; color is 20D.

*Pollen.*—Color is 23B.

*Fruit.*—Dry drupe, ovoid, 1 cm long and 0.8 cm in diameter.

*Fruit color.*—193C to 194D.

*Seeds per capsule.*—Typically single seed.

*Seed shape.*—Ovoid with acute apex and base.

*Seed dimensions.*—8 mm long and 5 mm in diameter.

*Color.*—Ranges between 165B and 166C.

Disease/pest resistance: No remarkable pest or discase resistance has been observed. It is expected that it will be susceptible to any pests or diseases that present major issue for the species.

I claim:

1. A new and distinct variety of *Styrax japonicus* plant named 'ORSTSTYx1', substantially as illustrated and described herein.

* * * * *